United States Patent [19]
Kambara et al.

[11] Patent Number: 5,922,912
[45] Date of Patent: *Jul. 13, 1999

[54] CONCENTRATION METHOD OF AQUEOUS ACRYLAMIDE SOLUTION

[75] Inventors: Yoshihiko Kambara; Mutsuo Matsumura; Michiaki Umeno; Yoshikazu Uehara; Koichi Asao, all of Osaka, Japan

[73] Assignee: Mitsui Chemicals, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/834,983

[22] Filed: Apr. 7, 1997

[30] Foreign Application Priority Data

Apr. 17, 1996 [JP] Japan ..................... 8-095332

[51] Int. Cl.$^6$ ................................. C07C 231/24
[52] U.S. Cl. .................. 564/206; 564/126; 564/127; 564/128; 564/204
[58] Field of Search ..................... 564/128, 127, 564/126, 204, 206

[56] References Cited

U.S. PATENT DOCUMENTS 3,917,693  11/1975  Asano et al. ..................... 564/127
3,923,741  12/1975  Asano et al. ..................... 564/206
3,941,837  3/1976   Asano et al. ..................... 564/127

FOREIGN PATENT DOCUMENTS 48-62713    9/1973   Japan .
48-62717    9/1973   Japan .
52-28777    7/1977   Japan .
54-106420   8/1979   Japan .
55-27048    7/1980   Japan .
55-27898    7/1980   Japan .
57-26587    6/1982   Japan .
60-12344    4/1985   Japan .
5-78293     3/1993   Japan .

*Primary Examiner*—Shailendra Kumar
*Attorney, Agent, or Firm*—Burns, Doane, Swecker & Mathis, L.L.P.

[57] ABSTRACT

A method is disclosed for the concentration of an aqueous acrylamide solution prepared by hydration of acrylonitrile or an aqueous acrylamide solution substantially free of acrylonitrile. The method makes use of a concentration apparatus at least a part of whose solution-contacting section is made of a copper-containing material. The concentration is conducted while introducing an oxygen-containing gas into the apparatus. Use of this method can prevent formation, adhering, accumulation and the like of popcorn polymers inside the concentration apparatus upon concentration of the aqueous acrylamide solution, and can also produce high-quality acrylamide.

11 Claims, 3 Drawing Sheets

CONCENTRATION METHOD OF AQUEOUS ACRYLAMIDE SOLUTION

BACKGROUND OF THE INVENTION

1. Field of the Invention

This invention relates to a concentration method of an aqueous acrylamide (hereinafter abbreviated as "AAM") solution, and especially to a concentration method featuring separation of unreacted acrylonitrile (hereinafter abbreviated as "AN") and excess water from a synthesis reaction mixture of AAM available through a hydration reaction from AN by a catalyst or a microorganism. This invention is also concerned with a concentration method of a dilute aqueous AAM solution which is substantially free of AN. More specifically, this invention pertains to an improved concentration method which makes it possible to obtain a dense aqueous AAM solution of good quality while preventing polymerization of AAM without addition of any polymerization inhibitor other than air.

2. Description of the Related Art

In the form of AAM-base polymers, AAM has been used for many years as papermaking chemicals, flocculants, oil recovery agents and the like. It also has a wide range of utility as a starting co-monomer for various polymers. For such utility, AAM was produced by the so-called sulfuric acid process previously. In recent years, processes making use of metal-copper-based catalysts or microorganisms have been developed and are industrially practiced these days. AAM is generally furnished as power or an aqueous solution to the market.

Upon production of an aqueous AAM solution through a catalytic hydration reaction of AN by a metal-copper-based catalyst, problems such as a reduction in the reaction velocity and by-production of impurities arise if the AN concentration in a feed solution is raised excessively or the conversion percentage in the reaction is increased too much. It is therefore the common practice to leave unreacted AN in a synthesis reaction mixture so that the concentration of AAM is limited to 20 to 40% or so. To convert the thus-obtained aqueous AAM solution into the commercial form of powder or an aqueous solution, it is necessary to remove unreacted AN and excess water from the synthesis reaction mixture so that the synthesis reaction mixture is concentrated to an aqueous AAM solution of a specified concentration. In some instances, it may also become necessary to concentrate a dilute aqueous AAM solution which is substantially free of AN.

In the course of such concentration, AAM is prone to polymerization, and an attempt to achieve a specified concentration tends to result in a product with AN still remaining therein without sufficient removal or in a low-quality product with AAM polymer mixed in a large amount. Concerning the concentration of an aqueous AAM solution, several methods have been proposed to date. In the case of concentration from a three-component system of AN-AAM-water, it is generally required to lower the concentration of remaining AN to 0.1% or lower in a concentrated solution. To this end, it is the common practice to use a distillation apparatus composed of a fractionation unit and a heat evaporation unit.

According to Japanese Patent Laid-Open No. 62713/1973, a distillation apparatus composed of a fractionation unit and a heating unit is employed. A solution to be distilled is caused to pass in the presence of a small amount of AN, which acts to suppress polymerization of AAM, through the fractionation unit. The solution is next caused to promptly evaporate in the heating unit, for example, by using a centrifugal-film evaporator, so that the small amount of AN is removed. This method is stated to be free from adhering and accumulation of gel-like polymer and also to permit sufficient removal of AN and provision of an aqueous AAM solution of a specified concentration, said solution containing polymer only in a trace amount.

Japanese Patent Publication No. 26587/1982 discloses a concentration method which makes no use of a fractionation tower for the removal of AN because such a fractionation tower induces polymerization of adhered AAM. Described specifically, subsequent to flash evaporation of a reaction mixture of AAM synthesis, said reaction mixture containing AN, AAM and water, the thus-evaporated reaction mixture is concentrated using a centrifugal-film evaporator in which the reaction mixture and evaporating steam are caused to flow countercurrently. This method is stated to permit sufficient removal of AN and also provision of an aqueous AAM solution of high concentration without occurrence of polymerization.

Concentration methods making use of oxygen-containing gases, such as air, as stabilizers are also disclosed. Japanese Patent Publication No. 27898/1980 discloses a concentration method. According to this method, a dilute aqueous AAM solution is fed to a concentration system composed of an oxygen gas absorption unit, a heating unit and a reduced-pressure evaporation unit. While recirculating a dense aqueous AAM solution in an amount 10 to 500 times as much as the thus-fed aqueous AAM solution through the units of the concentration system, oxygen is caused to dissolve in the aqueous solution in the oxygen gas absorption unit, the aqueous solution is heated to 20 to 60° C. in the heating unit to maintain a temperature difference between the feed solution to the evaporation unit and an effluent from the evaporation unit within a range of from 1 to 20° C., and water is then caused to evaporate off under reduced pressure.

Further, Japanese Patent Publication No. 28777/1977 discloses that the stability of a dilute aqueous AAM solution can be improved by adding at least one of the hydroxides, carbonates and bicarbonates of alkali metals.

Japanese Patent Laid-Open No. 78293/1993 discloses a method for concentrating a dilute aqueous AAM solution. This method makes use of a heating unit and a gas-liquid separator. The heating unit is maintained in a wet state, and the aqueous AAM solution is heated together with an oxygen-containing gas so that water is absorbed in the oxygen-containing gas.

Japanese Patent Laid-Open No. 62717/1973 discloses that an aqueous AAM solution of a specified concentration, which will develop no quality problem under high temperature and atmospheric pressure, can be obtained by adequately bringing air in an amount as much as 0.1 times or more in terms of moles of the water to be evaporated into contact with an aqueous AAM solution upon concentration of the last-mentioned aqueous AAM solution.

In contrast to the above-mentioned methods which make use of air as a stabilizer, methods featuring concentration in a non-oxidizing atmosphere are disclosed in Japanese Patent Publication No. 27048/1980 and Japanese Patent Publication No. 12344/1985.

Japanese Patent Laid-Open No. 106420/1979 discloses a concentration method in which attributing polymerization to oxygen which flows into a concentration apparatus, nitrogen monoxide is added in an amount of 4 moles or greater per mole of oxygen flowing into the apparatus so that oxygen-induced polymerization can be prevented.

According to the present inventors' knowledge and finding, polymerization can be prevented for the first time by allowing copper ions, which serve as a polymerization inhibitor, to exist at a high concentration, for example, of 100 ppm or more based on AAM upon conducting concentration in an non-oxidizing atmosphere without introduction of air as disclosed in Japanese Patent Publication No. 62717/1973 or Japanese patent Publication No. 12344/1985. Copper ions are removed in a purification step, but the use of copper ions at such a high concentration results in a substantial load to the purification step and is thus not preferred.

The method disclosed in Japanese Patent Laid-Open No. 106420/1979, which makes use of nitrogen monoxide as a polymerization inhibitor, is an effective method for the prevention of polymerization in a concentration step. However, when an AAM product concentrated and purified in accordance with this method was polymerized and the quality of the AAM product was evaluated based on the water solubility and ultimate molecular weight of the polymer, the results were not preferred. Moreover, use of nitrogen monoxide on a commercial scale is not practical for its high cost, toxicity and the like.

Methods for reducing the concentration of AN to a level of 0.1% or lower in a three-component system of AN-AAM-water are disclosed in Japanese Patent Laid-Open No. 62713/1973 and Japanese Patent Publication No. 26587/1982. These publications make no mention about polymerization inhibitors and therefore, these methods are considered to be effective only when a polymerization inhibitor such as copper ions exists at a high concentration.

The prevention of polymerization becomes very difficult when a solution with a polymerization inhibitor such as copper ions contained only at a low concentration is subjected to concentration by an apparatus composed of a heating unit and an AN-separating fractionation unit. Introduction of an oxygen-containing gas such as air has certain effects for the prevention of polymerization but, as the operation goes on, popcorn polymers adhere and accumulate especially in the fractionation unit, thereby making it difficult to continue the operation further.

Since polymers tend to occur and adhere in an AN-separating fractionation unit as described above, Japanese Patent Publication No. 26587/1982 discloses a concentration method which makes no use of a fractionation tower, that is, which performs concentration by using a centrifugal-film evaporator where a mixed solution and evaporating steam flow countercurrently. In this case, however, the separation of AN tends to become insufficient.

Concentration of a two-component system of AAM-water, which does not require separation of AN, is disclosed in Japanese Patent Publication No. 27898/1980, Japanese Patent Publication No. 28777/1977 and Japanese Patent Laid-Open No. 78293/1993. This system does not require any fractionation unit so that the concentration apparatus is composed of a heating unit and a reduced-pressure evaporation unit. In this respect, the methods are advantageous for the prevention of polymerization. According to the inventors' finding, however, unless a polymerization inhibitor such as copper ions existed at a high concentration, the introduction of an oxygen-containing gas such as air was still difficult to prevent polymerization so that popcorn polymers tended to adhere in the heating unit and the reduced-pressure evaporation unit.

As has been described above, the method featuring introduction of an oxygen-containing gas such as air as a polymerization inhibitor in a concentration apparatus instead of causing a polymerization inhibitor such as copper ions to exist at a high concentration have high tendency to induce adhering of popcorn polymers on walls of processing units such as heating unit, evaporation unit and fractionation unit. This adhering problem therefore still remains unresolved.

SUMMARY OF THE INVENTION

The present inventors have proceeded with an extensive investigation with a view to overcoming the problem of formation, adhering and accumulation of popcorn polymers which is encountered when concentrating a three-component system of AN-AAM-water or a two-component system of AAM-water by using only an oxygen-containing gas such as air as a polymerization inhibitor. As a result, it has been surprisingly found that use of a copper material in a solution-contacting section of a concentration apparatus can prevent the formation and adhering of popcorn polymers, leading to the completion of the present invention.

According to the present invention, there is thus provided a concentration method of an aqueous acrylamide solution, which comprises concentrating an aqueous acrylamide solution available by hydration of acrylonitrile or an aqueous acrylamide solution substantially free of acrylonitrile in a concentration apparatus at least a part of whose solution-contacting portion is made of a copper-containing material while introducing an oxygen-containing gas into the apparatus.

In a preferred embodiment of the present invention, the aqueous acrylamide solution available by the hydration of acrylonitrile may be concentrated. The apparatus may comprise a heat evaporator, a condenser, a vacuum equipment and a fractionation tower and optionally, a gas-liquid separator. In a solution-contacting section where the concentration of the acrylonitrile in the aqueous solution under the concentration is not higher than 1 wt. % based on the acrylamide in the same aqueous solution, the proportion of a surface area made of the copper-containing material may be at least 10% of a total surface area of the solution-contacting section.

In another preferred embodiment of the present invention, the aqueous acrylamide solution substantially free of acrylonitrile may be concentrated. The apparatus may comprise a heat evaporator, a condenser, a vacuum equipment and a gas-liquid separator. The proportion of a surface area of the copper-containing material may be at least 10% of a total surface area of solution-contacting sections in the heat evaporator, the gas-liquid separator and a piping connecting the heat evaporator and the gas-liquid separator together.

According to the method of the present invention, a dilute aqueous solution of AAM can be concentrated into a high-concentration solution free of AAM polymer only by introducing an oxygen-containing gas without any particular need for the addition of a polymerization inhibitor which makes difficult a purification step to be performed subsequent to the concentration. It is therefore possible to obtain a high-quality aqueous AAM solution having polymerization properties sufficient to furnish AAM products of high molecular weight and good water solubility.

DETAILED DESCRIPTION OF THE INVENTION AND PREFERRED EMBODIMENTS

Figure 1:
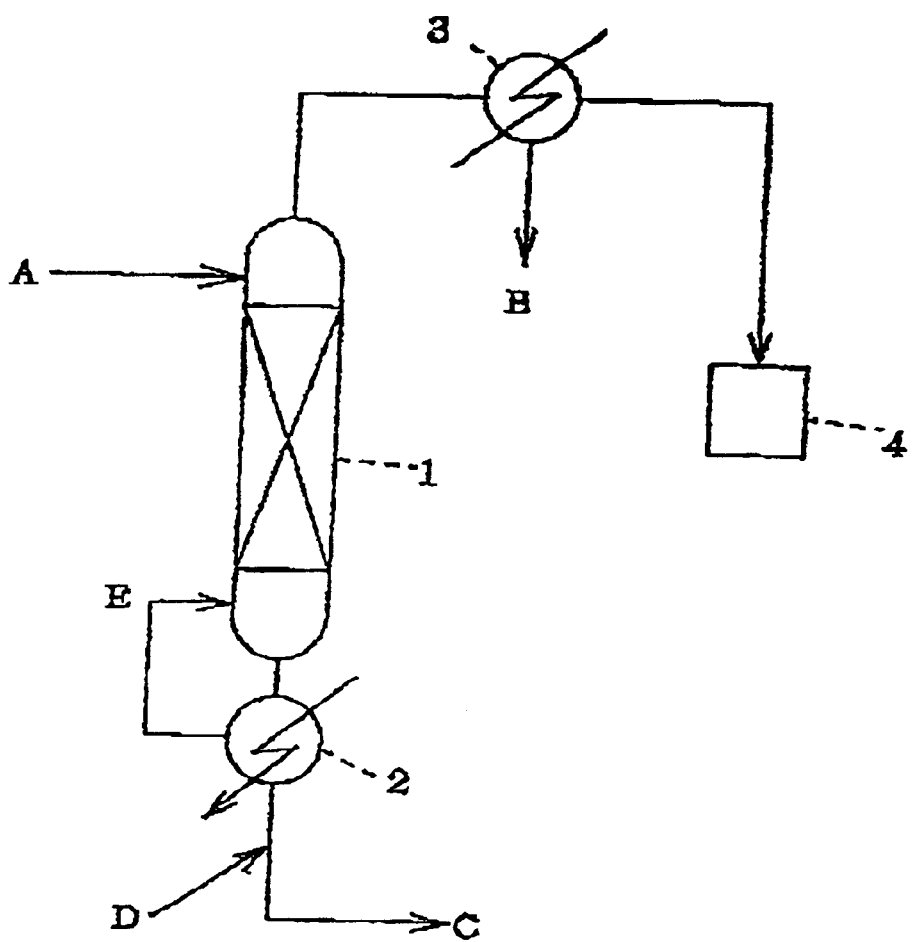
FIG. 1 is a flow diagram illustrating a concentration apparatus suited for use in the practice of a method according to one embodiment of the present invention.

The aqueous AAM solution, which is fed to the concentration apparatus in the present invention, is typically an aqueous AAM solution available from a liquid mixture of AN and water by subjecting the AN to a hydration reaction while using a catalyst or a microorganism.

Illustrative examples of the catalyst include metal oxides such as manganese oxide; and metals such as copper, cobalt and palladium. However, a metal-copper-base catalyst is generally employed for its highest superiority in activity and selectivity. Illustrative of the copper-base catalyst are Raney copper, reduced copper and Urushibara copper. These copper catalysts may additionally contain titanium, zinc, nickel, chromium and/or aluminum.

A hydration reaction by a copper-base catalyst is generally conducted as will be described next. As the manner of reaction, it is conducted in a flow-through manner, semi-batchwise or batchwise in a catalyst bed of the liquid-phase suspension type or the fixed bed type. The weight ratio of AN to water to be subjected to the hydration reaction is practically optional but may preferably be in a range of from 60:40 to 5:95, with a range of from 50:50 to 10:90 being more preferred. The conversion percentage of AN is optional but may preferably be in a range of from 10 to 98%, with a range of from 30 to 95% being more preferred. The reaction temperature in the hydration reaction between AN and water may preferably be in a range of from 40 to 200° C., with a range of from 60 to 150° C. being more preferred.

A reactor is internally maintained under a vapor pressure at the above-described temperature and composition or under a pressure of the vapor pressure plus a partial pressure of an inert gas such as nitrogen. This pressure generally ranges from atmospheric pressure to 10 atm. Dissolved oxygen, which is contained in a catalyst, AN, water and the like to be fed into the reactor, impairs the activity of the catalyst and increases by-products such as ethylene cyanohydrin. It is therefore desired to fully remove such dissolved oxygen before feeding them into the reactor. For the same reason, it is also desired to maintain the interior of the reactor under an oxygen-free atmosphere.

Incidentally, a reaction mixture which is taken out of the reactor after the hydration reaction is primarily composed of unreacted AN, excess water and AAM. As their weight proportions, AAM generally ranges from 10 to 40% or so, AN from 0 to 40% or so, and water from 40 to 90% or so. In addition, the reaction mixture also contains by-products such as ethylene cyanohydrin in trace amounts.

When a metal-copper-based catalyst is used as a catalyst, copper ions dissolve in the reaction mixture. Their concentration generally reaches about 1 to 40 ppm based on AAM although it varies depending on the reaction conditions, the catalyst and the like. When a cupric salt (Japanese Patent Publication No. 110514/1970) or cupric nitrate (Japanese Patent Publication No. 20294/1982) is used as a co-catalyst, dissolved cupric ions are contained as much as 100 ppm or higher, usually 150 to 400 ppm or so based on AAM.

Where a co-catalyst is used and copper ions are contained at a high concentration in the reaction mixture as described above, or when a polymerization inhibitor such as copper ions, thiourea or methoxyhydroquinone is added in a concentration step even where the concentration copper ions in the reaction mixture is low, the polymerization in the concentration step can be avoided by a known technique. It is however necessary to remove such a polymerization inhibitor in the subsequent purification step. The polymerization inhibitor gives an extra load to the purification step, and therefore is not preferred.

A first object of the present invention is to provide a concentration process in which a load to a purification step is extremely low. The present invention is therefore also effective for the concentration of a synthesis reaction mixture which is available in accordance with the microorganism method and contains no copper ions.

No particular limitation is imposed on the type of the concentration apparatus usable in the present invention. A general concentration apparatus is usable. The apparatus is composed of a heat evaporator, a condenser and a vacuum equipment, and if needed, a fractionation tower, a gas-liquid separator and the like for the separation of AN.

As the heat evaporator, a multipipe heat exchanger can be used in the form of a standard evaporator, a forced circulation evaporator, a rising thin film evaporator or a falling film evaporator as described, for example, on pages 404 to 405 of "Kagaku Kogaku Binran (Handbook of Chemical Engineering)", 4th edition, 1978, Maruzen Co., Ltd. Costly centrifugal-film evaporators have heretofore been used extensively for substances susceptible to thermal modifications or polymerization like AAM. Use of the method of the present invention however makes it possible to satisfactorily apply economical multipipe heat exchangers.

As the fractionation tower, either a packed tower or a tray tower is usable as desired. In general, however, packed towers are used widely for their small pressure losses.

Figure 2:
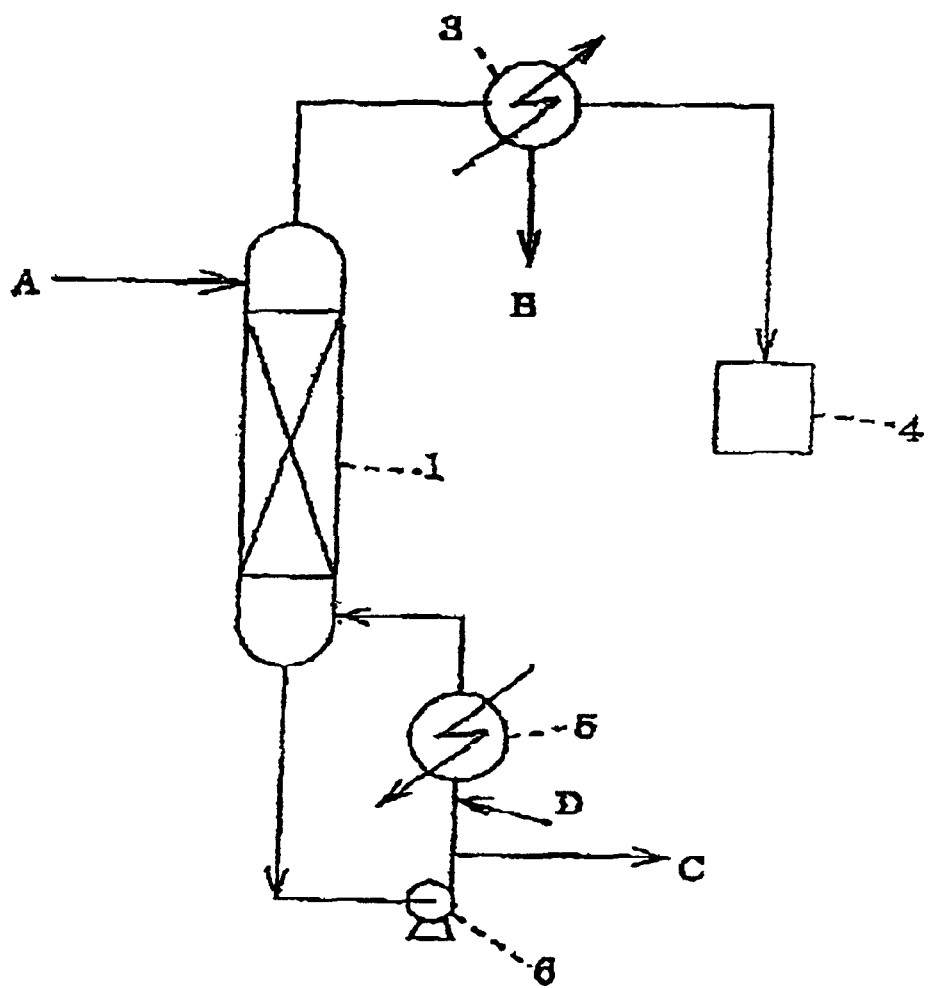
FIG. 2 is a flow diagram illustrating a concentration apparatus suited for use in the practice of a method according to another embodiment of the present invention.
Figure 3:
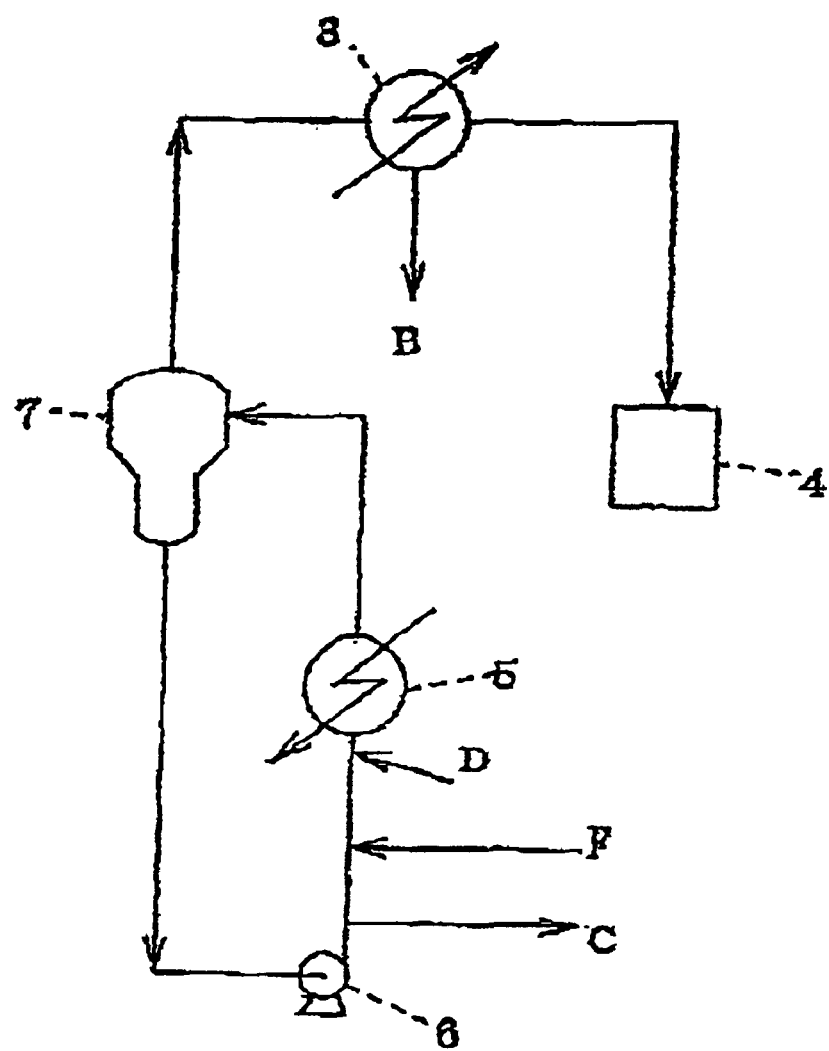
FIG. 3 is a flow diagram illustrating a concentration apparatus suited for use in the practice of a method according to a further embodiment of the present invention.

Examples of a concentration apparatus available from a combination of these units are shown in FIGS. 1 to 3.

In a concentration operation, a lower pressure leads to a lower temperature and is hence more advantageous for the prevention of polymerization. According to the conventional art, it was therefore common to perform concentration at 100 mmHg or lower. Such a low pressure however can achieve only low energy efficiency when conducting condensation with a cooling medium. The method of the present invention, however, does not require such a low pressure and can still sufficiently prevent polymerization even at a pressure as high as 130 to 250 mmHg or so.

No particular limitation is imposed on a heating medium for the heat evaporator, although steam or warm water is generally used. The smaller the temperature difference between the heating medium and the AAM solution, the more advantageous for the prevention of polymerization. A smaller temperature difference however results in the need for a greater area of heat-transfer surface. The method of the present invention makes it possible to set this temperature difference at 20 to 60° C., so that the heat evaporator can be reduced in size.

A second object of the present invention is to provide a concentration process which can produce high-quality AAM substantially free of AAM polymers under economical and easy operational conditions.

It is essential for the concentration apparatus for use in the present invention that at least a part of a member forming a solution-contacting section, with which an aqueous AAM solution is brought into contact, is made of a copper-containing material. Locations where the copper-containing material is required differ depending on the composition of the feed solution and the concentration procedures. They may however include, for example, heating surfaces of an evaporator, an inner wall and packing or trays of fractionation tower or a gas-vapor separator, said inner wall of said vapor-phase section having tendency to serve as a place where adhered droplets or mist tends to remain and polymerize, and piping connecting these units together. As a result of operation in a concentration apparatus made of stainless steel, locations susceptible to such polymer adhering and accumulation can be specified. A replacement of stainless steel by a copper-containing material at such locations makes it possible to confirm the prevention of such polymerization, so that the advantageous effects of the present invention can be clearly understood.

A more detailed description will now be made of locations where a copper-containing material is required in view of the composition of a feed solution and the procedures of concentration. An apparatus—which is adopted in connection with a step in which unreacted AN and excess water are separated from a synthesis reaction mixture to concentrate the synthesis reaction mixture into an aqueous AAM solution of a specified concentration—is generally constructed of a heat evaporator, a condenser, a vacuum equipment and a fractionation tower and optionally, a gas-liquid separator. As is described in Japanese Patent Laid-Open No. 26587/1982, AN acts to suppress the polymerization of AAM. Nonetheless, when the concentration of AN in an aqueous AAM solution under concentration drops to 1 wt. % or lower based on AAM, AAM becomes very susceptible to polymerization so that polymers tend to adhere and accumulate on walls of processing units. It is therefore preferred that the proportion of a surface area in a section made of the copper-containing material be at least 10% of a total area of a section with which such an aqueous AAM solution is brought into contact.

As the fractionation tower for the separation of AN, a packed tower is often employed. A packing within the tower has a very large solution-contacting surface area so that polymers highly tend to adhere and accumulate especially in a bottom portion where the concentration of AN drops to 1 wt. % or less based on AAM. Therefore, a packing in a section where the concentration of AN is 1 wt. % or less based on AAM is preferably made of a copper-containing material to an extent of 20% or more in terms of surface area.

An apparatus—which is adopted in connection with a step in which a dilute aqueous AAM solution substantially free of AN is concentrated to a specified concentration—is generally constructed of a heat evaporator, a condenser, a vacuum equipment and a gas-liquid separator. As polymerization tends to take place in all solution-contacting sections in this case, the proportion of a surface area of a copper-containing material is preferably at least 10% of the sum of inner surface areas of the heat evaporator, the gas-liquid separator and a piping connecting the heat evaporator and the gas-liquid separator together.

The term "copper-containing material" as used herein means a copper-based material generally employed as a structural material. Examples of the copper-containing material include oxygen-free copper; phosphorus-deoxidized copper; and copper alloys such as beryllium copper, red brass and brass. Among these, oxygen-free copper and phosphorus-deoxidized copper, which are high in purity, are most preferred. For the method of the present invention, introduction of an oxygen-containing gas into the concentration apparatus is essential. The concentration of oxygen in the oxygen-containing gas may range from 5 to 100% or so. Use of air is preferred from the standpoint of convenience. Concerning the amount of the oxygen-containing gas to be introduced, an excessively large amount is not preferred because such an excessively large amount results in exertion of substantial loads on the vacuum equipment and the condenser apparatus is discharged through the vacuum equipment. On the other hand, the oxygen-containing gas is unable to fully exhibit its polymerization-preventing effects when introduced in an unduly small amount. The amount of the oxygen-containing gas is preferably from 10 to 10,000 ppm, more preferably 50 to 1,000 ppm or so in terms of the weight ratio of oxygen to AAM. Such a limitation is not imposed when the oxygen-containing gas is brought into contact with an aqueous AAM solution before entering the concentration apparatus. No particular limitation is imposed on the location for the introduction insofar as oxygen is retained in a dissolved form in the aqueous AAM solution to be introduced into the heat evaporator.

Use of the concentration method of the present invention makes it possible to obtain, from an AAM synthesis reaction mixture containing copper ions at a concentration of 20 ppm or lower based on AAM and also containing unreacted AN and excess water, a high-quality aqueous AAM solution which contains AN at a concentration of 0.01 wt. % or lower and AAM at a specified concentration of 40 wt. % or higher, is substantially free of AAM polymers to such a degree as little as 0.001 wt. % or lower, and has polymerization properties sufficient to furnish AAM products of high molecular weight and good water solubility.

The present invention will next be described with reference to the accompanying drawings. It is to be noted that the present invention shall not be limited to the following examples unless a departure from its gist takes place.

Reference is first had to FIG. 1 which as a flow diagram, illustrates the concentration apparatus suited for use in the practice of the method according to one embodiment of the present invention. An AAM synthesis reaction mixture A containing unreacted AN and excess water is continuously fed to a top portion of a fractionation tower 1. The fractionation tower 1 is a packed tower, whereas a heat evaporator 2 is a centrifugal-film heat exchanger. Steam E, which has been produced in the presence of an oxygen-containing gas D in the heat evaporator 2 and consists primarily of water, is brought into countercurrent contact with the AAM synthesis reaction mixture A within the fractionation tower 1 so that AN is caused to evaporate into vapor. The AN vapor so separated is condensed and trapped at a condenser 3. The introduced oxygen-containing gas D flows through the heat evaporator 2, the fractionation tower 1 and the condenser 3 and is then discharged through a vacuum equipment 4. A concentrated solution C which has been processed to a specified AAM concentration owing to the removal of AN is processed further through a purification step into an aqueous AAM solution as a final product.

Reference is next had to FIG. 2 which as a flow diagram, illustrates the concentration apparatus suited for use in the practice of the method according to another embodiment of the present invention. In place of the centrifugal-film heat exchanger in FIG. 1, a multipipe heat exchanger is used as a forced circulation heat evaporator 5. By a circulating pump 6, a concentrated solution C is fed together with an oxygen-containing gas D to the heat evaporator 5, where the concentrated solution C is heated to give off steam. A portion of the circulating concentrated solution C is drawn out and is then fed to a purification step to obtain an aqueous AAM solution as a final product.

Reference is now had to FIG. 3 which as a flow diagram, illustrates the concentration apparatus suited for use in the practice of the method according to the further embodiment of the present invention. FIG. 3 is an illustrative flow diagram for concentrating a dilute aqueous AAM solution which is free of AN. Instead of the fractionation tower 1, a gas-liquid separator 7 is arranged. Steam, which has been produced as a result of heating in a heat evaporator 5, is separated by the gas-liquid separator 7 to obtain a concentrated solution C. If necessary, the concentrated solution C is processed further through a purification step into an aqueous AAM solution as a final product.

The present invention will hereinafter be described in further detail by the following examples. All designations of "part" or "parts" in the following examples mean part or parts by weight.

EXAMPLE 1

Referring to the flow diagram shown in FIG. 1, a synthesis reaction mixture A—which had been obtained from a reaction between AN and water in the presence of a metal-copper-based catalyst, contained 15 wt. % of AN and 30 wt. % of AAM and also contained copper ions at a concentration of 5 ppm based on AAM—was continuously fed at a rate of 100 parts per hour to the top of the fractionation tower 1 maintained under a reduced pressure of about 160 mmHg. The fractionation tower 1 was packed with copper-made Raschig rings. While introducing air D at a rate of 0.05 part per hour into the centrifugal-film evaporator 2 through a lower part thereof, a concentrated solution was heated with saturated steam of 100° C. In this case, the temperature difference from a concentrated solution was 37° C. The concentrated solution C was obtained at a rate of 60 parts per hour, which had the following composition: 50 wt. % AAM, 0.001 wt. % AN, and $\leq 0.001$ wt. % polymers. After being operated for 10 days, the concentration apparatus was disassembled for inspection. Adhering and accumulation of polymers were not observed. Incidentally, solution-contacting sections of the concentration apparatus were all made of SUS304 except for the copper-made Raschig rings. In this case, the proportion of a copper-made surface area was about 60% of the total surface area of sections with which a solution containing AN at a concentration not higher than 1 wt. % based on AAM was brought into contact.

REFERENCE EXAMPLE 1

The procedures of Example 1 were repeated likewise except that the Raschig rings in the fractionation tower 1 were changed from the copper-made ones to those made of SUS304 and copper sulfate was added to the feed synthesis reaction solution A to adjust the concentration of copper ions to 240 ppm based on AAM. To obtain at a rate of 60 parts per hour a concentrated solution C which had the following composition: 50 wt. % AAM, 0.001 wt. % AN, and $\leq 0.001$ wt. % polymers, operation was continued for 10 days. After the end of the operation, the concentration apparatus was disassembled for inspection. Only extremely slight adhering and accumulation of polymers was observed.

COMPARATIVE EXAMPLE 1

Concentration was conducted in a similar manner as in Example 1 except that the Raschig rings in the fractionation tower 1 were changed from the copper-made ones to those made of SUS304. The concentration went well for about 1 day after the start. However, the concentration of AAM polymers in a concentrated solution began to rise gradually and on the second day, the solution no longer flowed down from the fractionation tower 1. The concentration apparatus was disassembled for inspection. As a result, a great deal of popcorn polymers was found adhering in a lower section and packed section of the fractionation tower.

EXAMPLE 2

Referring to the flow diagram shown in FIG. 2, a synthesis reaction mixture A—which had been obtained from a reaction between AN and water in the presence of a metal-copper-based catalyst, contained 15 wt. % of AN and 30 wt. % of AAM and also contained copper ions at a concentration of 5 ppm based on AAM—was continuously fed at a rate of 100 parts per hour to the top of the fractionation tower 1 maintained under a reduced pressure of about 160 mmHg. The fractionation tower 1 was packed with copper-made Raschig rings. As the heat evaporator 5, a multipipe heat exchanger was used as a forced circulation evaporator. While circulating a concentrated solution at a rate of 1,000 parts per hour by the pump 6, air D was introduced at a rate of 0.05 part per hour and the concentrated solution was heated with saturated steam of 100° C. In this case, the temperature difference from the concentrated solution was 37° C. The concentrated solution C was obtained at a rate of 60 parts per hour, which had the following composition: 50 wt. % AAM, 0.001 wt. % AN, and $\leq 0.001$ wt. % polymers. After being operated for 10 days, the concentration apparatus was disassembled for inspection. Adhering and accumulation of polymers were not observed. Incidentally, solution-contacting sections of the concentration apparatus were all made of SUS304 except for the copper-made Raschig rings.

EXAMPLE 3

Concentration of Biosynthetically-Obtained Aqueous AAM Solution (1) Cultivation of Cells A sterilized culture medium of the below-descried composition was prepared in a manner known per se in the art, and was then inoculated with MT-10822 strain described in Japanese Patent Application No. 15295/1997 (which has already been deposited under the deposition number of FERM BP-5785 with National Institute of Bioscience and Human-Technology, Agency of Industrial Science and Technology). Following procedures known per se in the art, cultivation was conducted at 37° C. until the growth of the microorganism strain reached a stationary phase.

Composition of Culture Medium

| Bactoyeast extract | 5 parts |
|---|---|
| Bactotrypsin | 10 parts |
| Sodium chloride | 5 parts |
| Ferric sulfate heptahydrate | 0.04 part |
| Cobalt chloride dihydrate | 0.01 part |
| Ampicillin sodium | 980 parts |
| pH (regulated with KOH) | 7.5 |

By centrifugation, cells alone were separated from the cultured medium. Subsequent to washing the cells with physiological saline, centrifugation was conducted again so that about 10 parts of wet cells were obtained.

(2) Production of Aqueous AAM Solution

Suspended in 19,400 parts of purified water were 600 parts of wet cells which had been obtained by the same procedures as in the procedures (1). While gently stirring the suspension at 10° C., 6,000 parts of AN were continuously added over 20 hours at a rate of 300 parts per hour. After completion of the addition of the AN, an aging reaction was conducted at 10° C. for 5 hours. By using activated carbon, the cells and the liquid reaction mixture were separated from each other, whereby the reaction mixture was obtained in an amount of 25,400 parts. As a result of an analysis of the thus-obtained liquid reaction mixture, the concentrations of AAM and AN were found to be 31 wt. % and 120 ppm, respectively, and practically no copper ions were traced.

(3) Concentration

Referring to the flow diagram shown in FIG. 3, an aqueous AAM solution which had been obtained by the same procedures as in the procedures (2) was continuously fed at a rate of 100 parts per hour. As the heat evaporator 5, a multipipe heat exchanger equipped with copper-made heating pipes was used as a forced circulation evaporator. While circulating a concentrated solution at a rate of 1,000 parts per hour by the pump 6, air D was introduced at a rate of 0.05 part per hour and the concentrated solution was heated with saturated steam of 100° C. In this case, the temperature difference from the concentrated solution was 37° C. The heated solution and the evaporated steam were introduced into the gas-liquid separator 7 whose inner wall was entirely made of copper. The gas-liquid separator 7 was maintained under a reduced pressure of about 160 mmHg. The concentrated solution C was obtained at a rate of 50 parts per hour, which had the following composition: 50 wt. % AAM and ≦0.001 wt. % polymers. After being operated for 10 days, the concentration apparatus was disassembled for inspection. Adhering and accumulation of polymers were not observed. Incidentally, solution-contacting sections of the concentration apparatus were all made of SUS304 except for the copper-made heating pipes and the copper-made inner wall of the gas-liquid separator. In this case, the proportion of the whole copper-made surface area was about 50% of the total surface area of sections.

COMPARATIVE EXAMPLE 2

Concentration was conducted in a similar manner as in Example 3 except that the concentration apparatus was made of SUS304 in its entirety. Even shortly after the start of operation, the concentration of polymers in a concentrated solution was high, and in about half a day, the heat transfer ability of the heat evaporator 5 dropped substantially. The concentration apparatus was disassembled for inspection. As a result, a great deal of popcorn polymers was found to have adhered and accumulated centering around heating surfaces of the evaporator and a gas-phase portion adjacent a gas-liquid interface in the gas-liquid separator.

EXAMPLE 4

Concentration was conducted as in Example 3 except that the heating surfaces of the evaporator and the gas-phase portion adjacent the gas-liquid interface in the gas-liquid separator, where adhering of polymers was observed in Comparative Example 2, were made of copper. The results were similar to those obtained in Example 3. In this case, the proportion of the total copper-made surface area was about 20% of the total surface area of solution-contacting sections.

What is claimed is:

1. A concentration method of an aqueous acrylamide solution, which comprises concentrating an aqueous acrylamide solution prepared by hydration of acrylonitrile or an aqueous acrylamide solution substantially free of acrylonitrile in a concentration apparatus at least a part of whose solution-contacting portion is made of a copper-containing material while introducing an oxygen-containing gas into said apparatus wherein the amount of oxygen is 10 to 10,000 ppm in terms of the weight ratio of oxygen to acrylamide.

2. The method of claim 1, wherein said aqueous acrylamide solution prepared by the hydration of acrylonitrile contains copper ions at a concentration in a range of from 0 to 100 ppm based on the acrylamide in the corresponding aqueous solution.

3. The method of claim 1, wherein said aqueous acrylamide solution prepared by the hydration of acrylonitrile is concentrated; said apparatus comprises a heat evaporator, a condenser, a vacuum equipment and a fractionation tower and optionally, a gas-liquid separator; and in a solution-contacting section where the concentration of the acrylonitrile in said aqueous solution under said concentration is not higher than 1 wt. % based on the acrylamide in the same aqueous solution, the proportion of a surface area made of said copper-containing material is at least 10% of a total surface area of said solution-contacting section.

4. The method of claim 3, wherein said fractionation tower is a packed tower in which the proportion of a surface area of a packing is at least 20% of a total surface area of a solution-contacting section.

5. The method of claim 1, wherein said aqueous acrylamide solution substantially free of acrylonitrile is concentrated; said apparatus comprises a heat evaporator, a condenser, a vacuum equipment and a gas-liquid separator; and the proportion of a surface area of said copper-containing material is at least 10% of a total surface area of solution-contacting sections in said heat evaporator, said gas-liquid separator and a piping connecting said heat evaporator and said liquid separator together.

6. The method of claim 1, wherein the amount of oxygen is 50 to 1,000 ppm in terms of the weight ratio of oxygen to acrylamide.

7. The method of claim 2, wherein the concentration of copper ions in said aqueous acrylamide solution is 20 ppm or lower based on the acrylamide.

8. The method of claim 1, wherein the concentrated aqueous acrylamide solution contains acrylonitrile at a concentration of 0.01 wt. % or lower.

9. The method of claim 1, wherein the concentrated aqueous acrylamide solution contains acrylamide at a concentration of 40 wt. % or higher.

10. The method of claim 1, wherein the concentrated aqueous acrylamide solution contains acrylamide polymer at a concentration of 0.001 wt. % or lower.

11. The method of claim 1, wherein the concentrated aqueous acrylamide solution contains acrylonitrile at a concentration of 0.01 wt. % or lower, acrylamide at a concentration of 40 wt. % or higher and acrylamide polymer at a concentration of 0.001 wt. % or lower.

* * * * *